(12) United States Patent
Inada et al.

(10) Patent No.: US 6,624,417 B1
(45) Date of Patent: Sep. 23, 2003

(54) APPARATUS AND METHOD FOR JUDGING PLASTIC

(75) Inventors: Koji Inada, Osaka (JP); Shoji Fujii, Osaka (JP); Tatsumi Tamon, Osaka (JP); Koichi Motomura, Osaka (JP); Takeshi Takao, Osaka (JP); Ikkan Nishihara, Osaka (JP); Toshihiro Fujita, Osaka (JP)

(73) Assignee: Idec Izumi Corporation, Osaka (JP)

(*) Notice: Subject to any disclaimer, the term of this patent is extended or adjusted under 35 U.S.C. 154(b) by 93 days.

(21) Appl. No.: 09/857,376

(22) PCT Filed: Oct. 2, 2000

(86) PCT No.: PCT/JP00/06857

§ 371 (c)(1),
(2), (4) Date: Jun. 4, 2001

(87) PCT Pub. No.: WO01/25755

PCT Pub. Date: Apr. 12, 2001

(30) Foreign Application Priority Data

Oct. 4, 1999 (JP) ............................................. 11-282948

(51) Int. Cl.⁷ ............................................................ G01N 21/35
(52) U.S. Cl. .................................. 250/339.12; 250/343
(58) Field of Search ............................ 250/339.12, 343, 250/338.5, 339.11, 341.8; 209/3.1; 194/212

(56) References Cited

U.S. PATENT DOCUMENTS

| | | | | |
|---|---|---|---|---|
| 4,243,882 A | * | 1/1981 | Yasujima et al. | ............ 250/339 |
| 4,719,351 A | * | 1/1988 | Schoeller et al. | ............ 250/339 |
| 5,067,616 A | * | 11/1991 | Plester et al. | ................ 209/3.1 |
| 5,206,510 A | * | 4/1993 | Wolf et al. | ................. 250/339 |
| 5,318,172 A | * | 6/1994 | Kenny et al. | ............... 209/524 |
| 5,512,752 A | * | 4/1996 | Aikawa et al. | ........ 250/339.12 |
| 5,585,636 A | * | 12/1996 | Dollansky | .................... 250/343 |
| 6,433,338 B1 | * | 8/2002 | Nordbryhn et al. | .... 250/339.12 |

FOREIGN PATENT DOCUMENTS

| | | | | |
|---|---|---|---|---|
| DE | 4340795 A1 | * | 2/1995 | ......... B07C/5/342 |
| JP | 63-271683 | | 11/1988 | |
| JP | 6-3260 | | 1/1994 | |
| JP | 6-323831 | | 11/1994 | |
| JP | 9-304275 | | 11/1997 | |
| JP | 10-24414 | | 1/1998 | |

* cited by examiner

Primary Examiner—Constantine Hannaher
Assistant Examiner—Otilia Gabor
(74) Attorney, Agent, or Firm—McDermott, Will & Emery

(57) ABSTRACT

In a plastic identifying apparatus (1), a reference light (L1) and a detecting light (L2), each having a predetermined wavelength, are irradiated to an object to be identified (4), and the transmitted lights of the reference light (L1) and detecting light (L2) are received. A detecting value expressing the quantity of light received of the detecting light (L2) is divided by a reference value expressing the quantity of light received of the reference light (L1), to obtain a computed value, based on which performed is identification of plastic forming the object to be identified 4. The wavelength of the reference light (L1) is in a wavelength band (hereat, 1550 nm) in which the light absorptances of all the types of plastics are of the lowest level, and the wavelength of the detecting light (L2) is in a wavelength region (hereat, in the range of 1700 to 1760 run) in which the absorption wavelength bands of many plastics except for PET, such as HDPE, are present.

21 Claims, 12 Drawing Sheets

F I G . 5
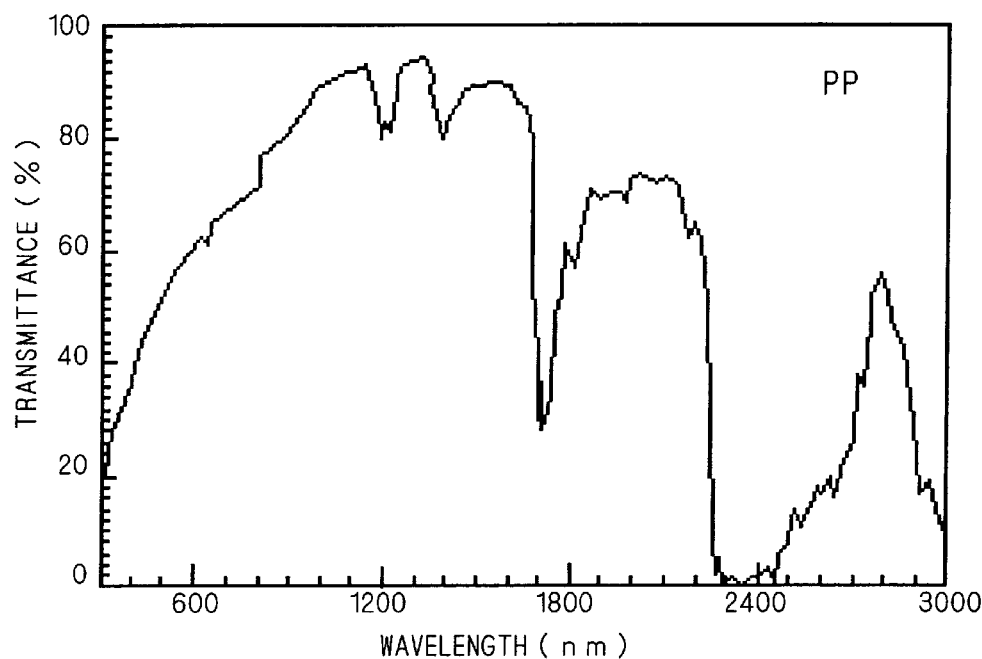
F I G . 6
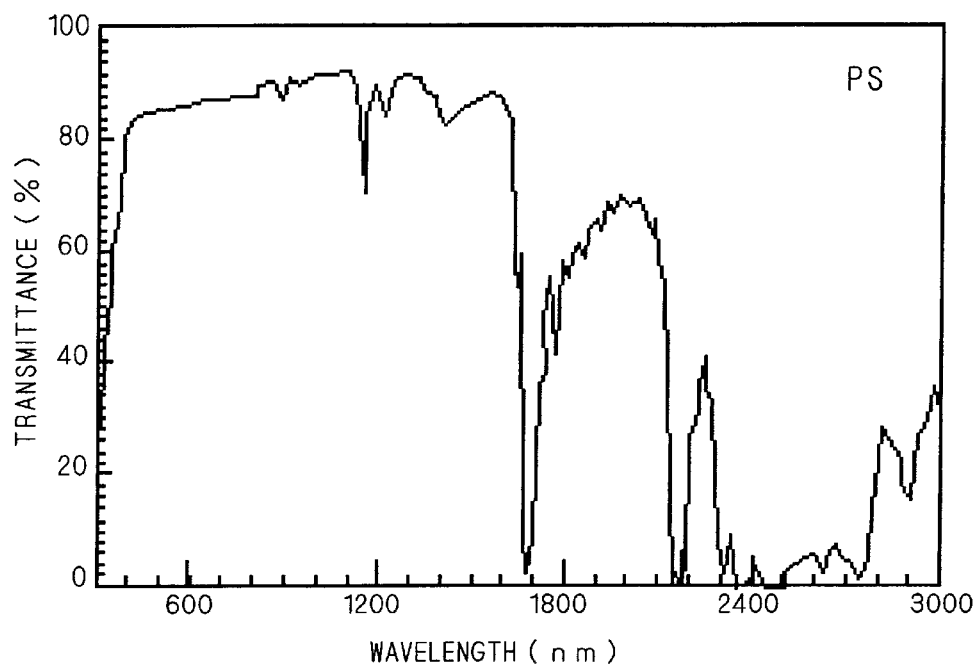

F I G . 7
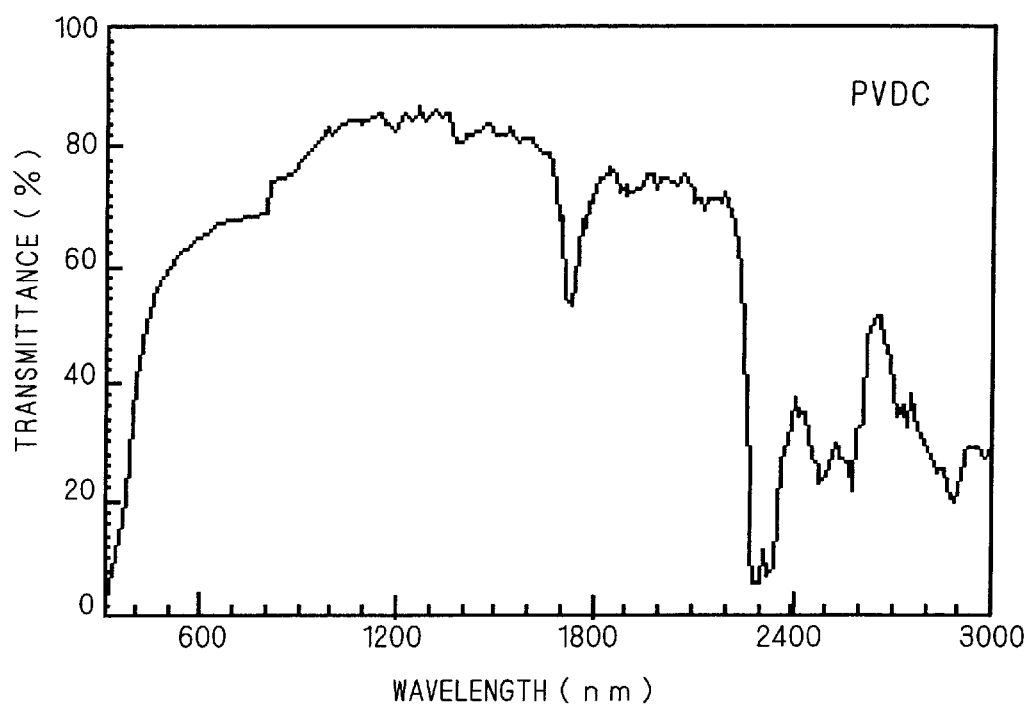

APPARATUS AND METHOD FOR JUDGING PLASTIC

TECHNICAL FIELD

This invention relates to a plastic identifying apparatus and a method thereof to identified by what type of plastic the object to be identified is formed.

BACKGROUND ART

In the recent years, the recycling of plastic products (especially PET bottles) has been proceeded. For efficient recycling, it is necessary to identify and sort plastic products depending on the type of their material, and it is being a theme how to conduct the identification of plastic products.

As a conventional plastic identifying apparatus using light, there is one in which near-infrared ray is irradiated to a plastic product while continuously changing the wavelength in the wavelength region of 1 to 2.5 $\mu$m, and the differential spectrum of its absorption spectrum is analyzed to identify the type of plastic forming the plastic product.

However, since in this conventional identifying apparatus it is necessary to irradiate near-infrared ray to plastic products while continuously changing the wavelength in the wavelength region of 1 to 2.5 $\mu$m, there is the problem that the optical system is complicated. Further, such a complicated processing of finding the differential spectrum is also needed in a signal processing after light receiving, and there are the problem that the apparatus construction and signal processing are complicated, and the problem that identification is time-consuming.

In addition, as regards the light source in this case, an incandescent lamp and mercury lamp are usually employed as one which emits near-infrared ray having a wavelength region of 1 to 2.5 $\mu$m. Hence, there is the problem due to the lifetime of the light source that its maintenance is laborious and the apparatus cost is increased as a whole.

In this conventional technique, there is a method in which no scanning of wavelength on the light source side is performed and an irradiation light having a wide wavelength region is irradiated from a light source and, when receiving the light, a wavelength selection is performed by using a spectral device such as grating. However, the problem of the light source lifetime is not solved, in addition to the fact that the cost is increased because the spectral device itself is extremely expensive.

DISCLOSURE OF INVENTION

It is a first object of this invention to provide a plastic identifying apparatus and a method thereof which enable to simplify the apparatus structure and signal processing and also attain a rapid identifying processing.

It is a second object of this invention to provide a plastic identifying apparatus and a method thereof, taking less time for maintenance.

Accordingly, in order to attain the above objects, this invention provides a plastic identifying apparatus (1, 21, 31, 41, 51) to identify by what type of plastic in predetermined plural types an object made of plastic to be identified (4) is formed, characterized by comprising a light source (2, 3, 3a, 3b) irradiating to said object to be identified a detecting light (L2, L2a, L2b) of which wavelength is in an absorption wavelength band to increase the light absorptance of at least one type of plastic in said plural types, and a reference light (L1) of which wavelength is different from said wavelength of said detecting light; a light receiving means (5, 5a, 5b, 5c) receiving a transmitted light or reflected light of said reference light and said detecting light from said object to be identified, and outputting a reference value expressing the quantity of light received of said reference light and a detecting value expressing the quantity of light received of said detecting light; and an identifying means (7) computing a proportion of or difference between said reference value and said detecting value, and identifying, based on the computed value, by what type of plastic in said plural types said object to be identified is formed.

Also, in order to attain the above objects, this invention provides a plastic identifying method of identifying by what type of plastic in predetermined plural types an object made of plastic to be identified (4) is formed, characterized by comprising the steps of: a light irradiating step of irradiating to said object to be identified, by a predetermined light source, a detecting light (L2, L2a, L2b) of which wavelength is in an absorption wavelength band to increase the light absorptance of at least one type of plastic in said plural types, and a reference light (L1) of which wavelength is different from said wavelength of said detecting light; a light receiving step of receiving by a predetermined light receiving means (5, 5a, 5b, 5c) a transmitted light or reflected light of said reference light and said detecting light from said object to be identified, and outputting to said light receiving means a reference value expressing the quantity of light received of said reference light and a detecting value expressing the quantity of light received of said detecting light; and an identifying step of computing a proportion of or difference between said reference value and said detecting value, and identifying, based on the computed value, by what type of plastic in said plural types said object to be identified is formed.

With this construction, it is unnecessary to scan the irradiation light in a predetermined wavelength region, as has been conventional, so that the apparatus construction such as of optical system and the signal processing after light receiving can be simplified, and a rapid identification can be attained.

Further, it is so arranged as to compute a proportion of or difference between a reference value expressing the quantity of light received of a reference light and a detecting value expressing the quantity of light received of a detecting light, and then perform identification based on the computed value. Therefore, the identification can be conducted by removing the unnecessary variable factor that varies depending on factors other than the type of plastic, for example, the shape of the object to be identified or the surface state such as dirt and damage. This leads to accurate identification.

Furthermore, in the case that identification is conducted by using the proportion of a reference value and a detecting value, when obtaining the proportion, the magnitude of the detecting value is standardized by the reference value. Therefore, there is the advantage that without specially standardizing the emission intensity and the like of a reference light and detecting light of a light source, the identification can be conducted irrespective of their setting conditions.

BRIEF DESCRIPTION OF DRAWINGS

FIG. 5 is a graph showing a light transmission property of polypropylene (PP).

FIG. 6 is a graph showing a light transmission property of polystyrene (PS).

FIG. 7 is a graph showing a light transmission property of polyvinylidene chloride (PVDC).

BEST MODE FOR CARRYING OUT THE INVENTION

First Preferred Embodiment

Firstly, based on FIGS. 1 to 10, description will proceed to a light absorbing property of plastic that is an example of objects to be identified, to which identification is conducted by a plastic identifying apparatus according to this preferred embodiment.

In the graphs of FIGS. 1 to 9, the abscissa indicates the wavelength of the light that is allowed to enter each plastic, and the ordinate indicates the light transmittance of the light of each wavelength to each plastic. That is, in the graphs of FIGS. 1 to 9, as the value of the ordinate of the graph is smaller, the light absorptance of each plastic is increased.

As the graphs of FIGS. 1 to 8 show, it is found that the absorption wavelength band in which the light absorptance of PET, HDPE, PVC, LDPE, PP, PS and PVDC falls within the infrared light region having a longer wavelength than 1600 nm. More specifically, the absorption wavelength band of HDPE, PVC, LDPE, PP and PVC is in the range of 1700 to 1760 nm, and the absorption wavelength band of PET and PS is substantially in the range of 1640 to 1700 nm.

On the other hand, from the graphs of FIGS. 1 to 7 and 9, it is found that in the range of 1500 to 1600 nm, the light absorptance of PET, HDPE, PVC, LDPE, PP, PS and PVDC translates approximately flat at substantially the lowest level.

Figure 11:
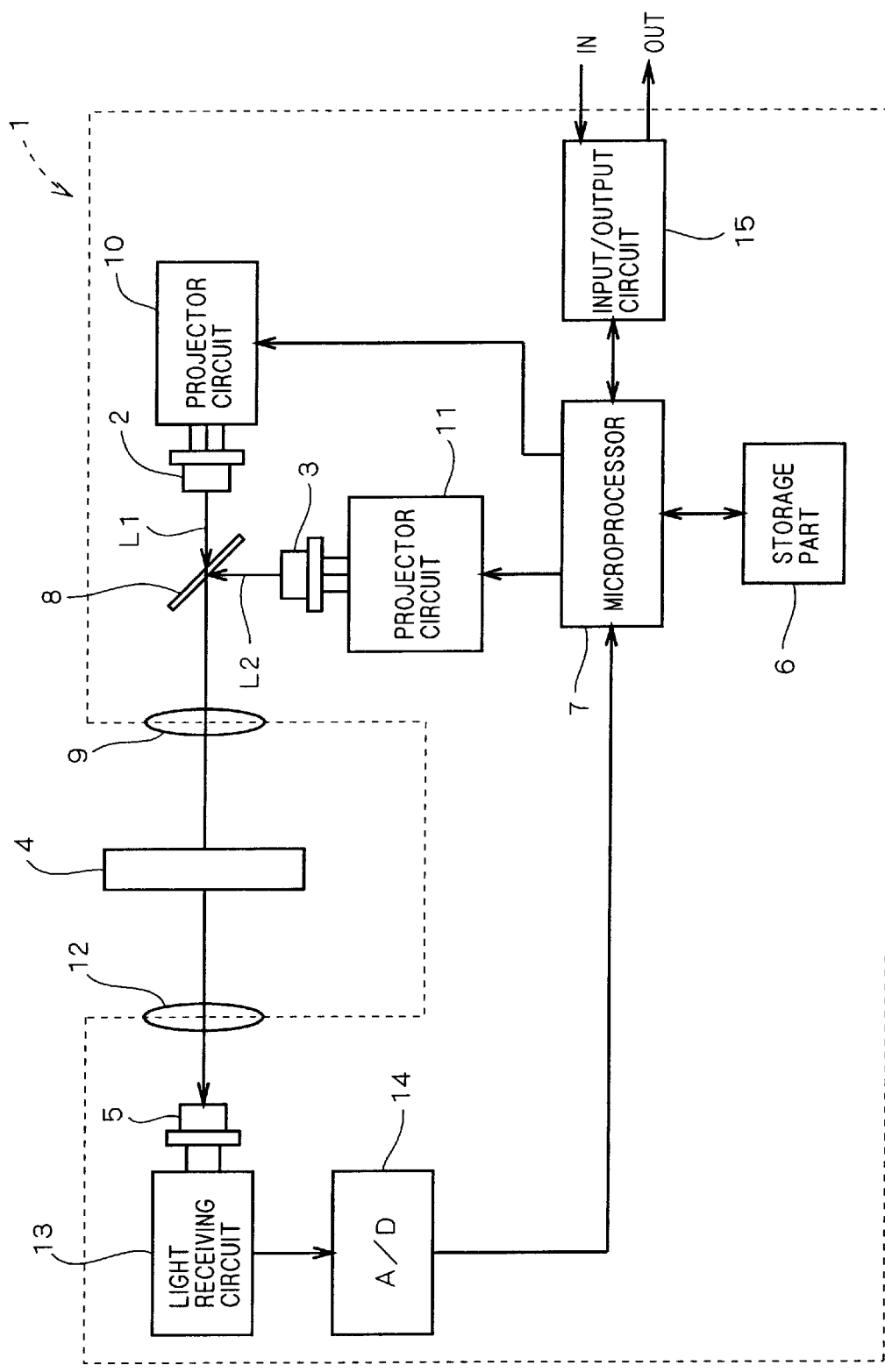
FIG. 11 is a diagram showing a construction of a plastic identifying apparatus according to a first preferred embodiment of this invention.

Thereby in the present preferred embodiment, the light of which wavelength is in the range of 1500 to 1600 nm is used as a reference light L1 serving as a reference (see FIG. 11). Also, the light of which wavelength is in the range of 1700 to 1760 nm or 1640 to 1700 nm is used as a detecting light L2 (see FIG. 11). The reference light L1 and detecting light L2 are irradiated to an object made of plastic to be identified (see FIG. 11), and the received light intensity of the transmitted light or reflected light of the detecting light L2 from the object 4 is divided by the received light intensity of the transmitted light or reflected light of the detecting light L2 from the object 4 and, based on the computed value thus obtained, the type of plastic forming the object 4 is identified.

Figure 1:
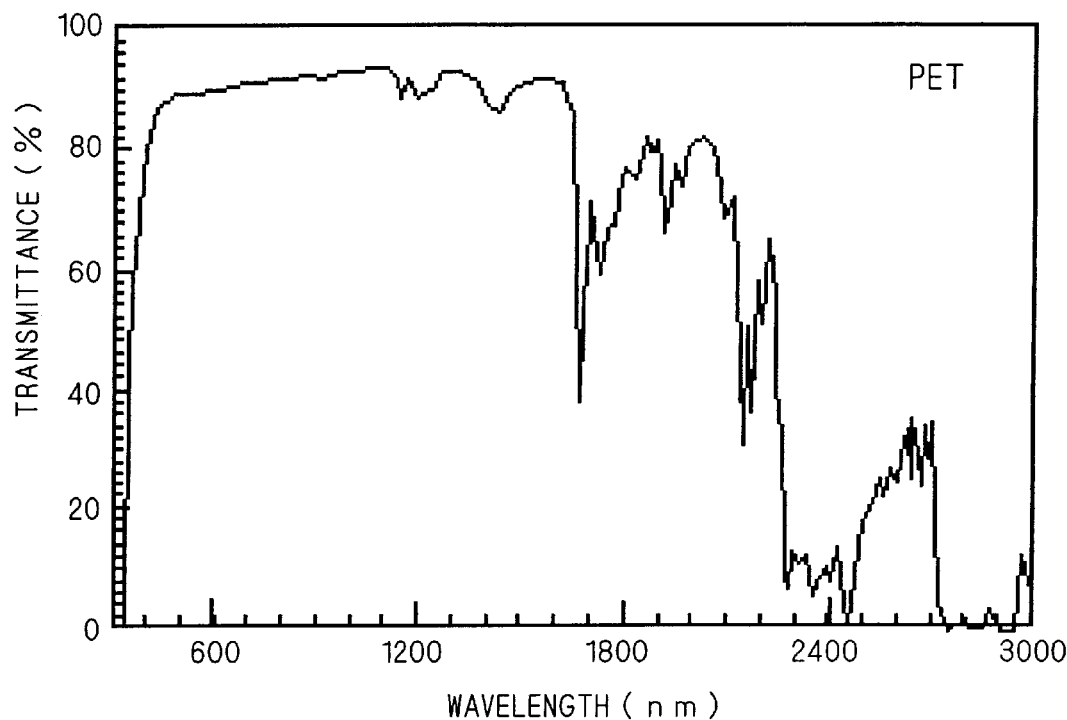
FIG. 1 is a graph showing a light transmission property of polyethylene terephthalate (PET).
Figure 2:
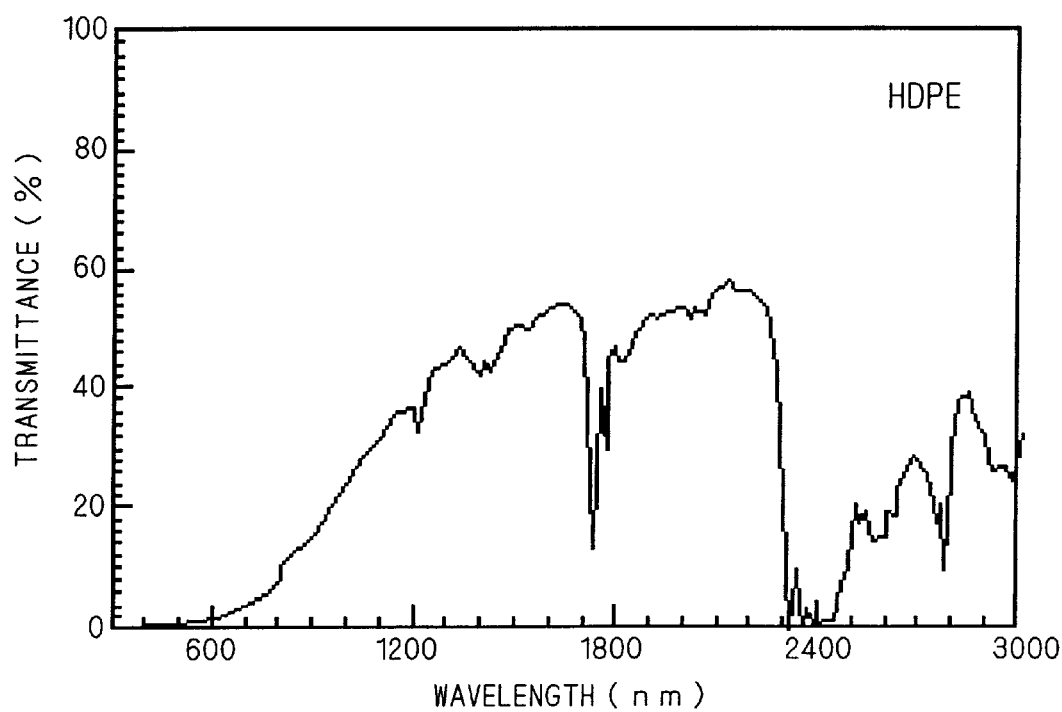
FIG. 2 is a graph showing a light transmission property of high-density polyethylene (HDPE).
Figure 3:
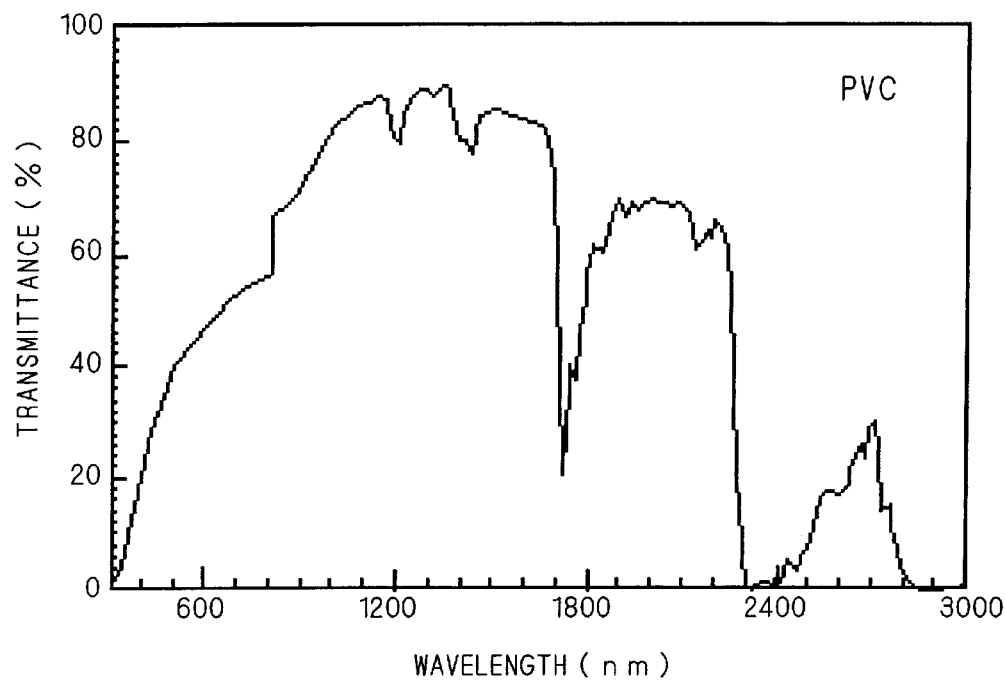
FIG. 3 is a graph showing a light transmission property of polyvinyl chloride (PVC).
Figure 4:
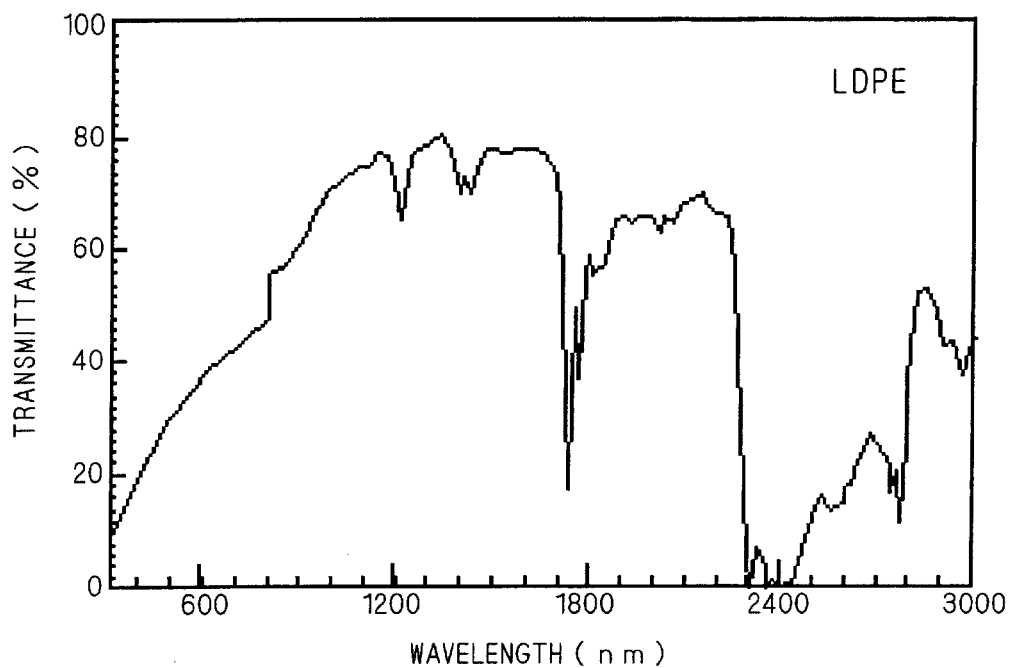
FIG. 4 is a graph showing a light transmission property of low-density polyethylene (LDPE).
Figure 8:
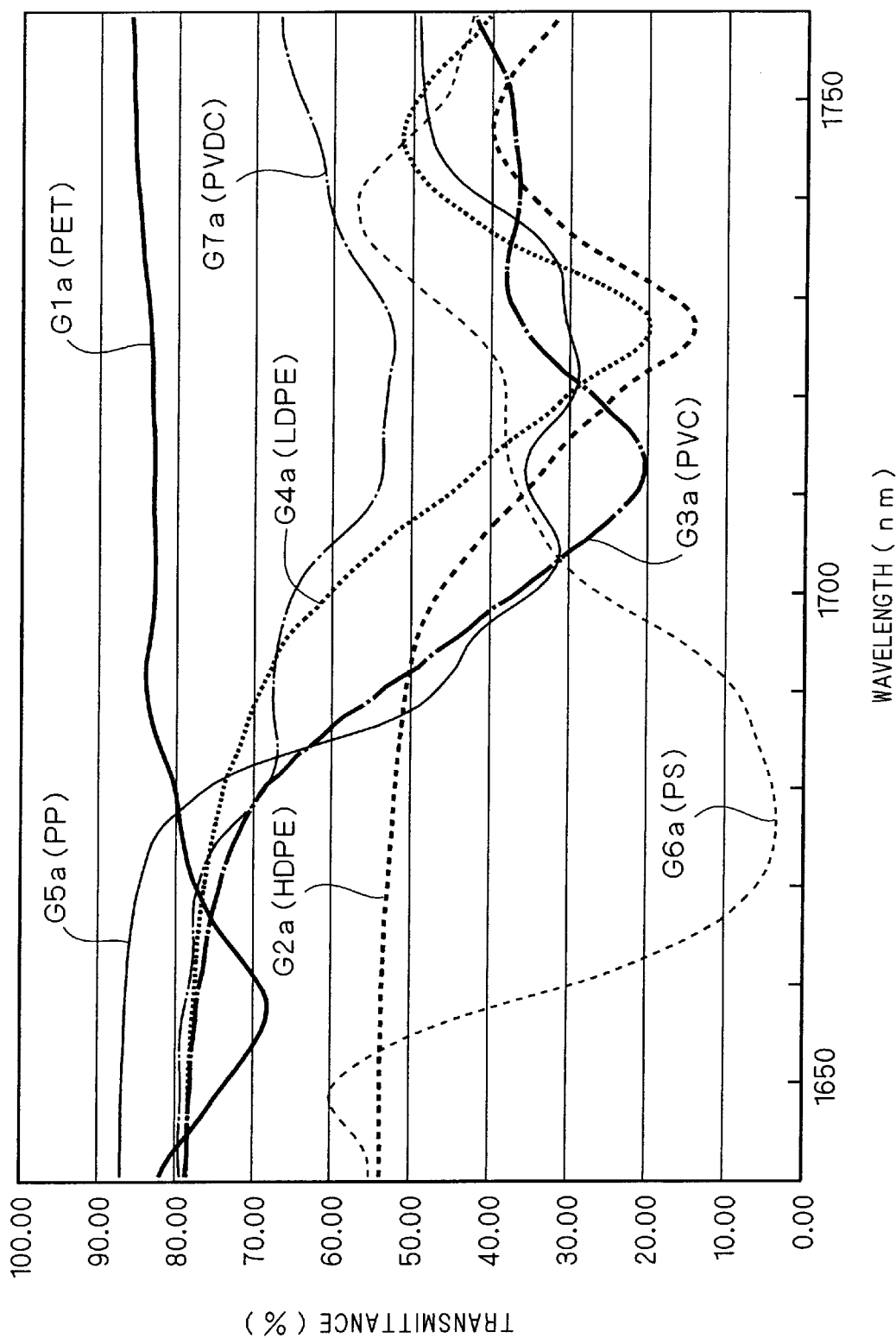
FIG. 8 is a diagram obtained by superposing the graphs shown in FIGS. 1 to 7, but showing in enlarged dimension the range of about 1650 to about 1750 nm.
Figure 9:
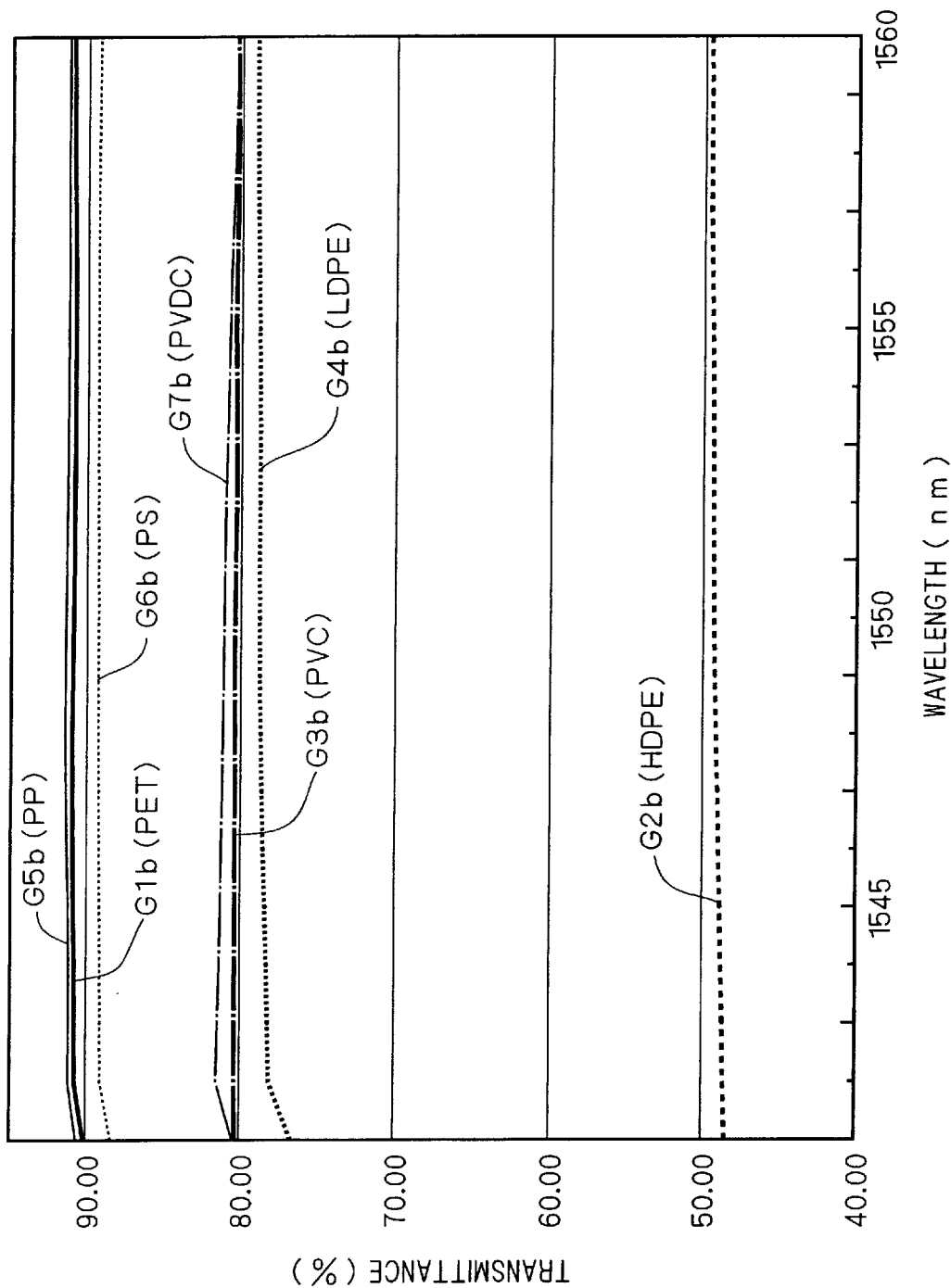
FIG. 9 is a diagram obtained by superposing the graphs shown in FIGS. 1 to 7, but showing in enlarged dimension the range of about 1540 to about 1560 nm.
Figure 10:
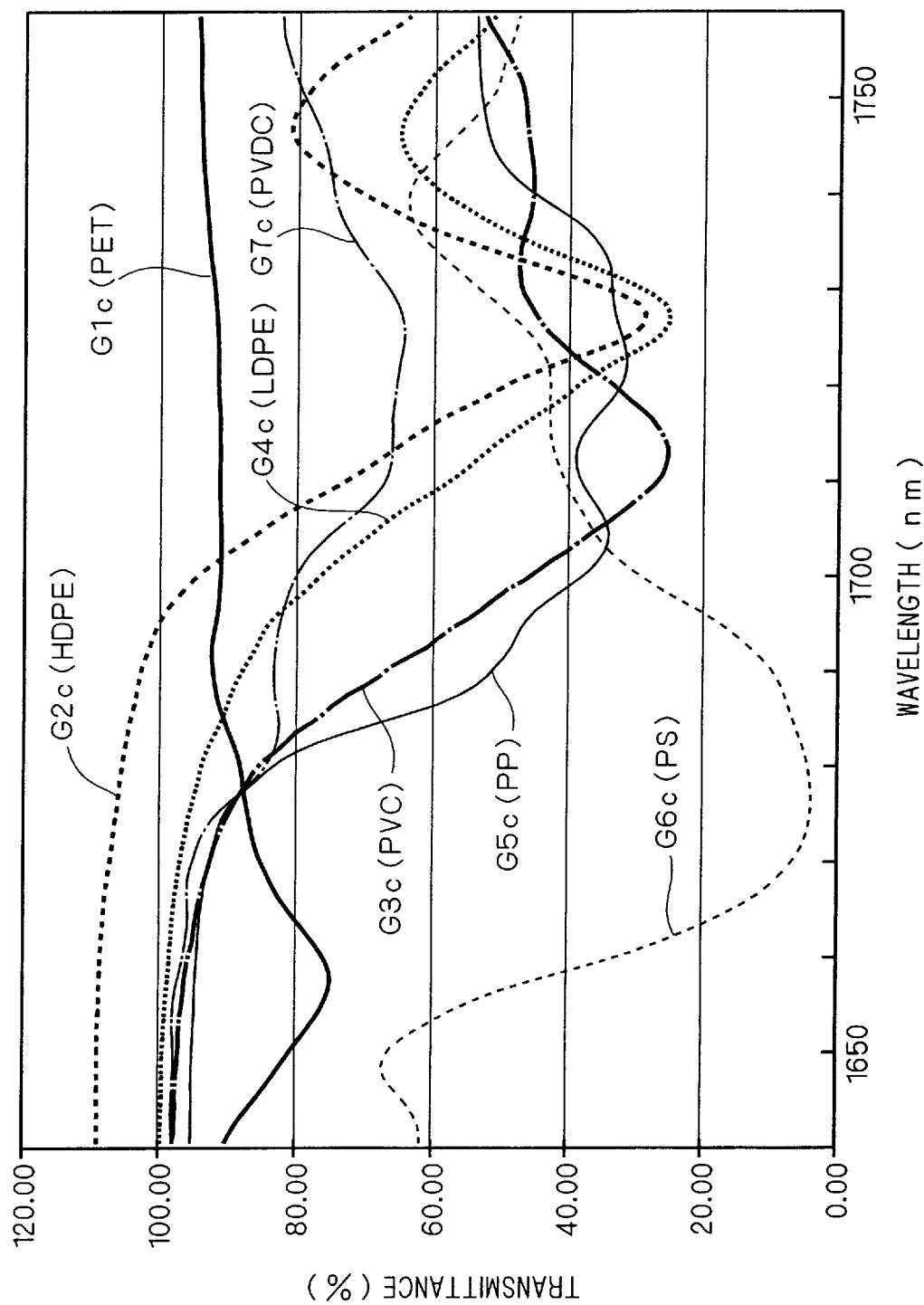
FIG. 10 is a graph showing the magnitude of light transmittance of each plastic at each wavelength when the light transmittance of each plastic at 1550 nm is taken as a reference (100%).

Hereat, the graphs G1c to G7c of FIG. 10 indicate the magnitude of the light transmittance of each plastic to each wavelength when the light transmittance of each plastic at 1550 nm is taken as a reference (100%).

A first preferred embodiment of this invention will next be described based on FIG. 11.

As shown in FIG. 11, the plastic identifying apparatus 1 comprises, as its main components, a semiconductor light-emitting device 2 irradiating a reference light L1, a semiconductor light-emitting device 3 irradiating a detecting light L2, a light receiving device (light receiving means) 5 receiving the reference light L1 and detecting light L2 from an object to be identified 4, a storage part (storing means) 6, and a microprocessor (identifying means) 7. Hereat, the semiconductor light-emitting devices 2 and 3 correspond to a light source according to this invention. The object to be identified 4 is to be one which is formed by one of the seven types of plastics as described above.

A laser diode capable of emitting light at a narrow wavelength width is used for the semiconductor light-emitting elements 2 and 3, and an InGaAsP laser diode is used especially for the semiconductor light-emitting device 3.

The semiconductor light-emitting device 2 irradiates the reference light L1 of which wavelength is in the range of 1500 to 1600 nm, toward the object to be identified 4. The peak wavelength of the reference light L1 is set to about 1550 nm. The reference light L1 emitted by the semiconductor light-emitting device 2 is irradiated via a dichroic mirror 8 and a lens 9 to the object to be identified 4. As the dichroic mirror 8, there is used one which selectively allows passage of light having a wavelength of 1550 nm. Although the dichroic mirror 8 is used herein as a means for efficiently interpose the optical axes of the reference light L1 and detecting light L2, other means such as a prism or grating may be used. Alternatively, only for the purpose of interposing the optical axis of the reference light L1 and the optical axis of the detecting light L2, a half mirror may be used instead of the dichroic mirror 8.

The semiconductor light-emitting device 3 irradiates the detecting light L2 of which wavelength is in the range of 1700 to 1760 nm, toward the object to be identified 4. The wavelength width of the detecting light L2 is here set to the vicinity of 1715 to 1735 nm. The detecting light L2 emitted by the semiconductor light-emitting device 3 is reflected from the dichroic mirror 8 so that its optical axis matches the optical axis of the reference light L1, and then irradiated via the lens 9 to the object to be identified 4.

These semiconductor light-emitting devices 2 and 3 are driven by projector circuits 10 and 11, and are drivingly controlled by the microprocessor 7 via the projector circuits 10 and 11.

The light receiving device 5 successively receives via a lens 12 the transmitted light of the reference light L1 and detecting light L2 from the object to be identified 4, and outputs an electric signal indicating the output value according to the quantity of the light received. The electric signal outputted from the light receiving device 5 is inputted to the microprocessor 7 via a light receiving circuit 13 and an A/D converting circuit 14. In the plastic identifying apparatus 1, it is arranged such that the reference light L1 and detecting light L2 are successively emitted at different timings. In response to this, the light receiving device 5 successively receives the transmitted light of the reference light L1 and detecting light L2 from the object to be identified 4, and it successively outputs an electric signal indicating a reference value corresponding to the quantity of light received of the reference light L1 and an electric signal indicating a detecting value corresponding to the quantity of light received of the detecting light L2.

A plurality of reference values that respectively correspond to plural types of plastics previously selected are stored in the storage part 6. Hereat, there are stored seven reference values that correspond to PET, HDPE, PVC, LDPE, PP, PS and PVDC, respectively.

In response to a distinguished command to be inputted via an input/output circuit 15, the microprocessor 7 allows the semiconductor light-emitting device 2 via the projector circuit 10 to light up in the form of pulses for a predetermined short time, thereafter, allows via the projector circuit 11 the semiconductor light-emitting device 3 to light up in the form of pulses for a predetermined short time, while reading, via the light receiving circuit 13 and AID converting circuit 14, the reference value and detecting value which are successively outputted from the light receiving device 5 in synchronization therewith.

Then the microprocessor 7 divides the detecting value with the reference value and judges to which reference value in the plural reference values stored in the storage part 6 the computed value is the closest, thereby it is identified by which plastic in the above-mentioned seven types plastics the object to be identified 4 is formed. That is, it is judged that the object to be identified 4 is formed by the plastic that corresponds to the reference value being the closest to the computed value in the plural reference values. The result of identification is outputted to the exterior via the input/output circuit 15.

Hereat, it may be arranged such that in determining to which reference value the computed value is the closest, a plurality of reference ranges corresponding to their respective reference values are previously provided and the closest reference value is determined by judging within which reference range the computed value falls.

The plural reference values stored in the storage part 6 may employ the result of measurement in another apparatus, alternatively, the result of measurement in the plastic identifying apparatus 1.

In the case of employing the result of measurement in another apparatus, it is necessary to prepare a reference value and input it into the plastic identifying apparatus 1. This will be described in order. Firstly, by such another apparatus, a reference light L1 and a detecting light L2 are irradiated in order toward a plurality of objects to be identified 4 formed by the respective types of plastics, and the transmitted light (or reflected light) of the reference light L1 and detecting light L2 from the objects to be identified 4 are received, thereby obtaining a reference value and a detecting value expressing the quantity of the light received of the reference light L1 and detecting light L2, respectively. The detecting value is then divided by the obtained reference value to prepare a plurality of reference values that correspond to the respective types of plastics. The prepared plural reference values are associated with the respective types of plastics and then inputted via the input/output circuit 15 to the plastic identifying apparatus 1. The inputted plural reference values are associated with the respective types of plastics and then recorded in the storage part 6 by the microprocessor 7.

Whereas in the case of employing the result of measurement in the plastic identifying apparatus 1 as a reference value, it is necessary to perform teaching to the plastic identifying apparatus 1. When performing the teaching, it is necessary that the plastic identifying apparatus 1 is switched from the normal mode for performing plastic identification to a teaching mode by inputting a mode switching command via the input/output circuit 15. This teaching is conducted as follows. Like the above-mentioned plastic identifying case, by the plastic identifying apparatus 1, a reference light L1 and a detecting light L2 are irradiated to objects to be identified 4 formed by the respective types of plastics, to receive the transmitted light of the reference light L1 and detecting light L2 from the objects to be identified 4, and the detecting value corresponding to the detecting light L2 is divided by the reference value corresponding to the reference light L1, to prepare a plurality of reference values that correspond to the respective types of plastics. The prepared plural reference values are associated with the plural types of plastics and then stored in the storage part 6. The return from the teaching mode to the normal mode is performed by inputting a return command via the input/output circuit 15. Such a teaching processing is performed by the control of the microprocessor 7.

The plastic identifying apparatus 1 thus constructed is installed on an identifying processing line, etc., for identifying plastic products such as of a recycling processing facility or the like, and is utilized for identifying plastic products. In this case, the plastic identifying apparatus 1 is connected to a central control unit controlling the line, so that it successively performs identifying processing in response to an identifying command provided from the central control unit, and successively outputs the result of identification to the central control unit.

Specifically, when an identifying command is provided from the central control unit to the plastic identifying apparatus 1, a reference light L1 and a detecting light L2 are successively irradiated to the object to be identified 4 by the semiconductor light-emitting devices 2 and 3, and the transmitted light of the reference light L1 and detecting light L2 from the object to be identified 4 are received by the light receiving device 5. Then, electric signals indicating a reference value expressing the quantity of the light received of the reference light L1 and a detecting value expressing the quantity of the light received of the detecting light L2 are inputted to the microprocessor 7 via the light receiving circuit 13 and A/D converting circuit 14.

By the microprocessor 7, the detecting value is divided by the reference value, and it is judged to which reference value of the plural reference values stored in the storage part 6 the computed value is the closest. Thereby, the type of plastic forming the object to be identified 4 is identified and its result is outputted to the central control unit via the input/output circuit 15.

As described above, according to this preferred embodiment, a reference light L1 and a detecting light L2, each having a predetermined wavelength, are irradiated to the object to be identified 4, and the transmitted light of the reference light L1 and detecting light L2 from the object to be identified 4 are received to perform identification. Therefore, it is unnecessary to scan an irradiation light within a predetermined wavelength region, as has been conventional, so that the apparatus construction such as of optical system and the signal processing after light receiving can be simplified, and a rapid identification can be attained.

Further, the identification is conducted based on the value obtained by dividing the detecting value expressing the quantity of the light received of the detecting light L2 by the reference value expressing the quantity of the light received of the reference light L1. Therefore, the identification can be conducted by removing the unnecessary variable factor that varies depending on factors other than the type of plastic, for example, the shape of the object to be identified 4 or the surface state such as dirt and damage. This enables to conduct accurate identification.

The detecting value is divided by the reference value and the magnitude of the detecting value is standardized by the reference value. Therefore, there is the advantage that without specially standardizing the emission intensity and the like of the reference light L1 and detecting light L2 of the semiconductor light-emitting devices 2 and 3, the identification can be conducted irrespective of their setting conditions.

Since in this preferred embodiment the semiconductor light-emitting devices 2 and 3 having a long lifetime are used as a light source, it is substantially unnecessary to replace the light source, thus requiring less time in maintenance.

Further, in this preferred embodiment, a semiconductor laser device is used for the semiconductor light-emitting devices 2 and 3. Since the semiconductor laser device emits a light at a narrow wavelength width, the emitted light can be directly irradiated to the object to be identified 4, without passing through a filter for wavelength selection. As a result, the light source construction can be simplified, and the waste of energy consumption is avoidable.

Since the wavelength of the reference light L1 falls within a wavelength region in which all the types of the plastics in the above-mentioned seven types have the lowest level of light absorptance (hereat, in the range of 1500 to 1600 nm), it is able to increase a difference between a reference value corresponding to the reference light L1 and a detecting value corresponding to the detecting light L2. Thereby, the computed value obtained by dividing the detecting value by the reference value can be changed at a large variable width according to the difference of the corresponding type of plastic, and the identification can be conducted easily and accurately.

In this preferred embodiment, the light of which peak wavelength is about 1550 nm is used for the reference light L1. Since this wavelength band is used for optical communication, there is the advantage that it is easy to purchase semiconductor light-emitting devices.

Further, the light of which wavelength is in the range of 1700 to 1760 nm (hereat, the light of which wavelength width is in the vicinity of 1715 to 1735 nm) is used for the detecting light L1. Since in the wavelength region of 1700 to 1760 nm, the absorption wavelength band of HDPE, PVC, LDPE, PP and PVD are within the range of 1700 to 1760 nm, it is easy to identify PET and PS, of which absorption wavelength band does not fall within this wavelength region, from HDPE, PVC, LDPE, PP and PVDC.

Second Preferred Embodiment

Figure 12:
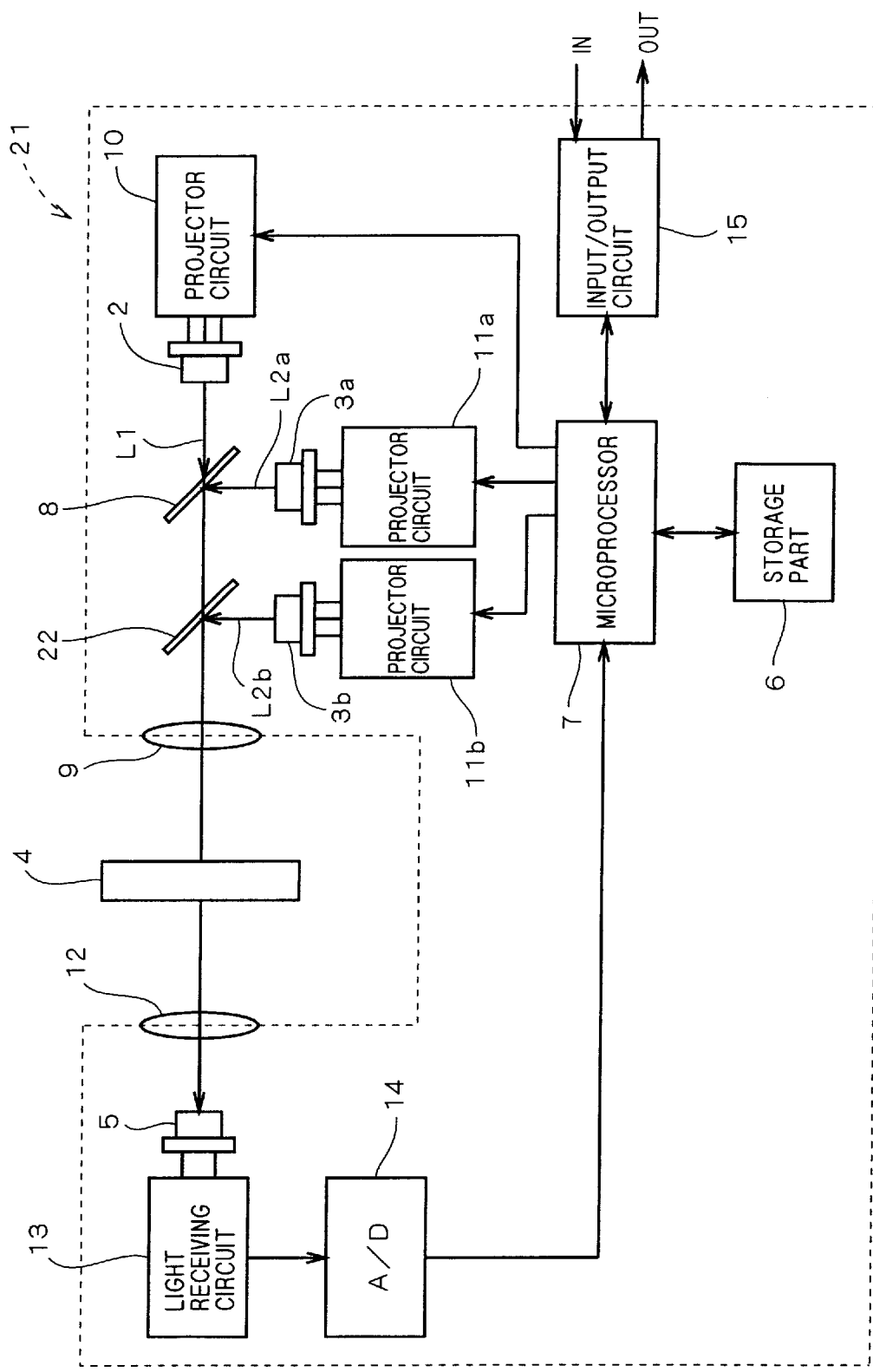
FIG. 12 is a diagram showing a construction of a plastic identifying apparatus according to a second preferred embodiment of this invention.

A plastic identifying apparatus according to a second preferred embodiment will next be described based on FIG. 12. In the construction of FIG. 12, the same reference numerals have been used for the parts corresponding to the construction of FIG. 11, and its description is omitted.

In a plastic identifying apparatus 21 according to this preferred embodiment, two semiconductor light-emitting devices 3a and 3b to irradiate detecting lights L2a and L2b having different wavelengths, respectively, are provided instead of the semiconductor light-emitting device 3 according to the first preferred embodiment. The semiconductor light-emitting devices 3a and 3b are drivingly controlled by a microprocessor 7 via projector circuits 11a and 11b. A semiconductor laser device is used for the semiconductor light-emitting devices 3a and 3b.

The semiconductor light-emitting device 3a is the same as the semiconductor light-emitting device 3 of the first preferred embodiment, and it irradiates a first detecting light L2a being the same as the detecting light L2 of the first preferred embodiment, toward an object to be identified 4.

In this preferred embodiment, along with the installation of the semiconductor light-emitting device 3b, a dichroic mirror 22 is disposed between a dichroic mirror 8 and a lens 9. The reference light L1 transmitted from the dichroic mirror 8 and the first detecting light L2a reflected from the dichroic mirror 8 are transmitted from the dichroic mirror 22 and then irradiated via the lens 9 to the object to be identified 4.

The semiconductor light-emitting device 3b irradiates a detecting light L2b of which wavelength is in the range of 1640 to 1700 nm to the object to be identified 4. Hereat, the wavelength width of the detecting light L2b is set to the vicinity of 1650 to 1670 nm. The second detecting light L2b emitted by the semiconductor light-emitting device 3b is reflected from the dichroic mirror 22 so that its optical axis matches the optical axes of the reference light L1 and the first detecting light L2a, and is irradiated via the lens 9 to the object to be identified 4.

A light receiving device 5 successively receives via a lens 12 the transmitted light of the reference light L1 from the object to be identified 4 and the transmitted light of the detecting lights L2a and L2b from the object to be identified 4, and then successively outputs an electric signal indicating a reference value expressing the quantity of the light received of the reference light L1, an electric signal indicating a first detecting value expressing the quantity of the light received of the first detecting light L2a, and an electric signal indicating a second detecting value expressing the quantity of the light received of the second detecting light L2b.

In a storage part 6, a plurality of reference values that respectively correspond to plural types of plastics selected in advance, as shown in the following Table 1 and Table 2, are associated with the respective types of plastics and stored for each of the detecting lights L2a and L2b. A group of reference values shown in Table 1 corresponds to the first detecting light L2a, and a group of reference values shown in Table 2 corresponds to the second detecting light L2b.

TABLE 1

| Type | PET | HDPE | PVC | LDPE | PP | PS | PVDC |
|---|---|---|---|---|---|---|---|
| Maximum | 96.62 | 31.28 | 48.22 | 27.21 | 35.26 | 53.14 | 68.78 |
| Middle | 92.02 | 29.8 | 45.92 | 25.91 | 33.58 | 50.6 | 65.51 |
| Minimum | 87.42 | 28.31 | 43.62 | 24.62 | 31.9 | 48.07 | 62.23 |

TABLE 2

| Type | PET | HDPE | PVC | LDPE | PP | PS | PVDC |
|---|---|---|---|---|---|---|---|
| Maximum | 71.63 | 56.24 | 81.09 | 81.54 | 90.83 | 37.72 | 82.56 |
| Middle | 68.22 | 53.56 | 77.23 | 77.66 | 86.5 | 35.92 | 78.63 |
| Minimum | 64.81 | 50.88 | 73.37 | 73.78 | 82.18 | 34.12 | 74.7 |

Hereat, seven groups of reference values that respectively correspond to PET, HDPE, PVC, LDPE, PP, PS and PVDC are previously stored for each of the detecting lights L2a and L2b. Each group of reference values is made up of middle value, maximum value and minimum value. The maximum value and minimum value are, as will be described hereinafter, those which indicate an allowance error range when a microprocessor 7 compares the computed values corresponding to the detecting lights L2a and L2b, respectively, with each reference value (hereat, each middle value), thereby performing plastic identification. Taking the middle value as a reference, the maximum value and minimum value are set to a value of plus or minus several % (hereat, plus or minus 5%) of the middle value.

It should be noted that in the allowance error ranges of the respective types of plastics shown in Table 1, the allowance error range of PVC (43.62 to 48.22) and the allowance error range of PS (48.07 to 53.14) are partially overlapped with each other in the range of 48.07 to 48.22. This is because at the wavelength band of the first detecting light L2a, PVC and PS are similar to each other in light absorptance. It is therefore difficult to perform accurate identification between PVC and PS, only by the first detecting light L2a.

Accordingly, in this preferred embodiment, as will be described hereinafter, a first computed value obtained by dividing the first detecting value corresponding to the first detecting light L2a by the reference value, falls within such a region in which a plurality of allowance error ranges corresponding to the first detecting light L2a are overlapped with each other (hereat, in the range of 48.07 to 48.22), no identification using the first computed value is performed within that region, but the identification is performed by using a second computed value obtained by dividing the second detecting value corresponding to the second detecting light L2b by the reference value.

Although in this preferred embodiment the allowance error range is set to plus or minus 5% of the middle value, thus causing such overlapping of the allowance error range, the above-mentioned seven types of plastics may be capable of being identified only by the first detecting light L2a, by increasing the accuracy of measurement and setting the allowance error range so as to be narrower (e.g., plus or minus 3% of the middle value).

In response to a distinguished command to be inputted via an input/output circuit 15, the microprocessor 7 allows the semiconductor light-emitting devices 2, 3a and 3b, via the projector circuits 10, 11a and 11b, to light up in the form of pulses for a predetermined short time, while reading, via the light receiving circuit 13 and A/D converting circuit 14, the reference value and detecting value which are successively outputted from the light receiving device 5 in synchronization therewith.

Then the microprocessor 7 divides the first and second detecting values by the reference value, to obtain first and second computed values, and performs identification based on the first and second computed values and the stored data of the storage part 6, and then outputs the result of identification to the exterior via the input/output circuit 15.

The operation of this identification will be described in detail. When the first computed value is not in the range of 48.07 to 48.22, it is judged to which middle value in a plurality of middle values corresponding to the respective plastics shown in Table 1 the first computed value is the closest. Thereby, it is judged by which plastic in the above-mentioned plural types of plastics the object to be identified 4 is formed. Alternatively, as a modification of this case, the judgment of type may be performed by judging within which allowance error range in the plural allowance error ranges corresponding to the respective plastics shown in Table 1 the first computed value falls.

On the other hand, when the first computed value is in the range of 48.07 to 48.22, it is judged to which of the middle value corresponding to PVC (77.23) and the middle value corresponding to PS (35.92) shown in Table 2 the first detecting value is closer. Thereby, it is judged by which of PVC and PS the object to be identified 7 is formed. Alternatively, as a modification of this case, it is judged within which of the allowance error range corresponding to PVC (73.37 to 81.09) and the allowance error range corresponding to PS (34.12 to 37.72) the second detecting value falls. Thereby, it is judged by which of PVC and PS the object to be identified 7 is formed.

As described above, according to this preferred embodiment, the following effects are obtainable in addition to the effects according to the first preferred embodiment.

That is, according to this preferred embodiment, identification is performed by using the second detecting light L2b of which wavelength is in the range of 1640 to 1700 nm, besides the first detecting light L2a of which wavelength is in the range of 1700 to 1760 nm. Therefore, when in the wavelength band of the first detecting light L2a, the light absorptance of plural plastics (hereat, PVC and PS) are alike to make it difficult to perform accurate identification merely by the first detecting light L2a, such plastics can be identified accurately by using the second detecting light L2b.

Modifications

Modification of the plastic identifying apparatus 1 and 21 (particularly the plastic identifying apparatus 21) of the foregoing first and second preferred embodiments will next be described based on FIG. 13. In the foregoing plastic identifying apparatus 21 and the like, the semiconductor light-emitting devices 2, 3a and 3b are arranged to successively light up, whereas in a plastic identifying apparatus 31 according to this modification, there are disposed light receiving devices 5a, 5b and 5c so as to correspond to semiconductor light-emitting devices 2, 3a and 3b, respectively, and the semiconductor light-emitting devices 2, 3a and 3b are arranged to light up at the same time.

Figure 13:
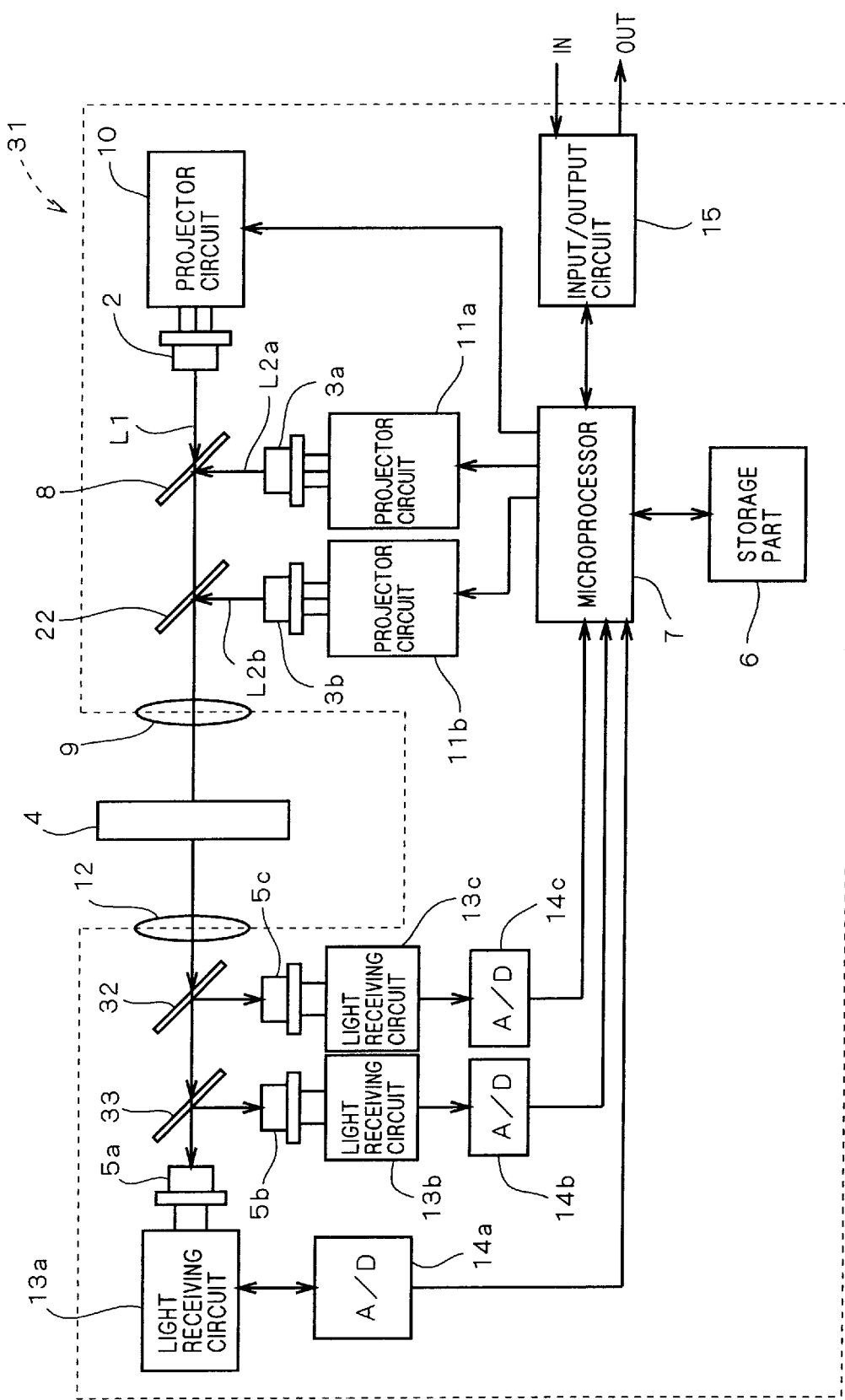
FIG. 13 is a diagram showing a modification of the plastic identifying apparatus according to the first and second preferred embodiments.

In the construction of FIG. 13, first and second dichroic mirrors 32 and 33 are disposed on a light receiving optical path at the back of a light receiving lens 12. A reference light L1, after passing through an object to be identified 4 to the apparatus 31 via the light receiving lens 12, passes through the two dichroic mirrors 32 and 33 and is received by a light receiving device 5a. Similarly, a first detecting light L2a entered into the apparatus 31 via the light receiving lens 12 passes through the first dichroic mirror 32 and is reflected from the second dichroic mirror 33 and received by a light receiving device 5b. Similarly, a second detecting light L2b entered into the apparatus 31 via the light receiving lens 12 is reflected from the first dichroic mirror 32 and received by a light receiving device 5c. The output signals outputted from the light receiving devices 5a to 5c are inputted to a microprocessor 7 via light receiving circuits 13a to 13c and A/D converting circuits 14a to 14c, which are disposed so as to correspond to the light receiving devices 5a to 5c, respectively. If required, dichroic mirrors that respectively correspond to the wavelengths of the reference light L1 and the detecting lights L2a and L2b, are disposed in the light receiving devices 5a, 5b and 5b.

Although the examples shown in FIGS. 11 to 13 show the case that the plastic identifying apparatuses 1, 21 or 31 is integrally constructed into one unit, the plastic identifying apparatuses 1, 21 or 31 may be constructed separately into plural (e.g., two) units, such as a projector unit and a light receiving unit. In this case, for example, the projector unit is provided with projector devices 2, 3, 3a, 3b, projector circuits 10, 11, 11a, 11b, and dichroic mirrors 8, 22, and lens 9 in the components shown in the identifying apparatuses 1, 21 or 31, and the light receiving unit is provided with components other than these components in the components shown in the identifying apparatuses 1, 21 or 31.

Other modifications of the plastic identifying apparatuses 1 and 21 according to the foregoing first and second preferred embodiments will next be described based on FIGS. 14 and 15. The foregoing plastic identifying apparatuses 1 and 21 employ a transmission type optical system, whereas plastic identifying apparatuses 41 and 51 according to the modifications of FIGS. 14 and 15 employ a reflection type optical system.

Specifically, in the plastic identifying apparatus 41, a half mirror 42 is disposed on the optical path between a dichroic mirror 8 and a lens 9, and the reflected lights of a reference light L1 and detecting light L2 from an object to be identified 4, which have been irradiated to the object to be identified 4 via the half mirror 42 and lens 9, are received via the lens 9 and reflected from the half mirror 42 and then received by a light receiving device 5. In the plastic identifying apparatus 51, a half mirror 42 is disposed on the optical path between a dichroic mirror 22 and a lens 9.

When light is irradiated to an object to be identified 4, part of the light is reflected from the surface of the object to be identified 4 while the rest enters the interior of the object to be identified 4. Part of the entered light is absorbed by the object to be identified 4 and the rest passes through the object to be identified 4, alternatively, it is reflected due to scattering in the interior of the object to be identified 4. Accordingly, the quantity of light of the reflected light from the object to be identified 4 that is obtained when an irradiation light of a predetermined wavelength and a predetermined quantity of light is irradiated to the object to be identified, varies with the rate that the object to be identified 4 absorbs the irradiation light according to the wavelength of the irradiation light. It is therefore possible to identify plastics based on the quantity of light of the reflected light from the object to be identified 4.

Although the plastic identifying apparatus 41 employs a coaxial optical system in which the optical axis of the irradiation light toward the object to be identified 4 and the optical axis of the reflected light received from the object to be identified 4 are set on the same axis, it may employ a different-axial optical system in which the optical axis of the irradiation light and the optical axis of the reflected light are set on different axes.

In the forgoing first and second preferred embodiments, the correction of each detecting value is made by dividing each detecting value by the reference value. As a still another modification, the correction of each detecting value may be made by obtaining a difference between each detecting value and the reference value.

In the foregoing second preferred embodiment, the plastic identification is conducted by using two detecting lights L2a and L2b. As a still another modification, the plastic identification may be conducted by using three or more detecting lights that respectively have the wavelengths corresponding to the absorption wavelength bands of the above-mentioned plastics.

Although in the foregoing first and second preferred embodiments, identification is conducted with respect to seven types of plastics, it may be arranged so as to identify in an alternative fashion, namely, whether an object to be identified 4 is formed by PET or other type of plastic.

In connection with this point, in the wavelength range of 1700 to 1760 nm, the light absorptance of PET translates at a low level, whereas HDPE, PVC, LDPE, PP and PVDC holds its absorption wavelength band. In the range of 1640 to 1700 nm, PET and PS holds its absorption wavelength band, and the light absorptance of PS translates at a higher level than PET, and the light absorptance of the plastics of HDPE, PVC, LDPE, PP and PVDC translates at a low level. Therefore, by using a detecting light of which wavelength is in the range of 1700 to 1760 nm or 1640 to 1700 nm, PET can be easily and accurately identified from other plastics.

Although in the foregoing first and second preferred embodiments, it is constructed so as to perform only plastic identification, a color sensor for optically detecting the color of the object to be identified 4 may be added to perform plastic identification and color detection at the same time. Thereby, plastic identification and color detection can be conducted by one apparatus.

Although in the foregoing first and second preferred embodiments, the coaxial optical system in which the reference light L1 and the detecting lights L2, L2a and L2b are irradiated on the same axis, the different-axial optical system may be employed.

As a still other modification of the plastic identifying apparatuses 1, 21 and 31 shown in FIGS. 11 to 13, an optical fiber is interposed on the optical path between the projector lens 9 and light receiving lens 12, and the object to be identified 4, the irradiation light and transmitted light on the optical path therebetween may be transferred by the optical fiber.

Figure 14:
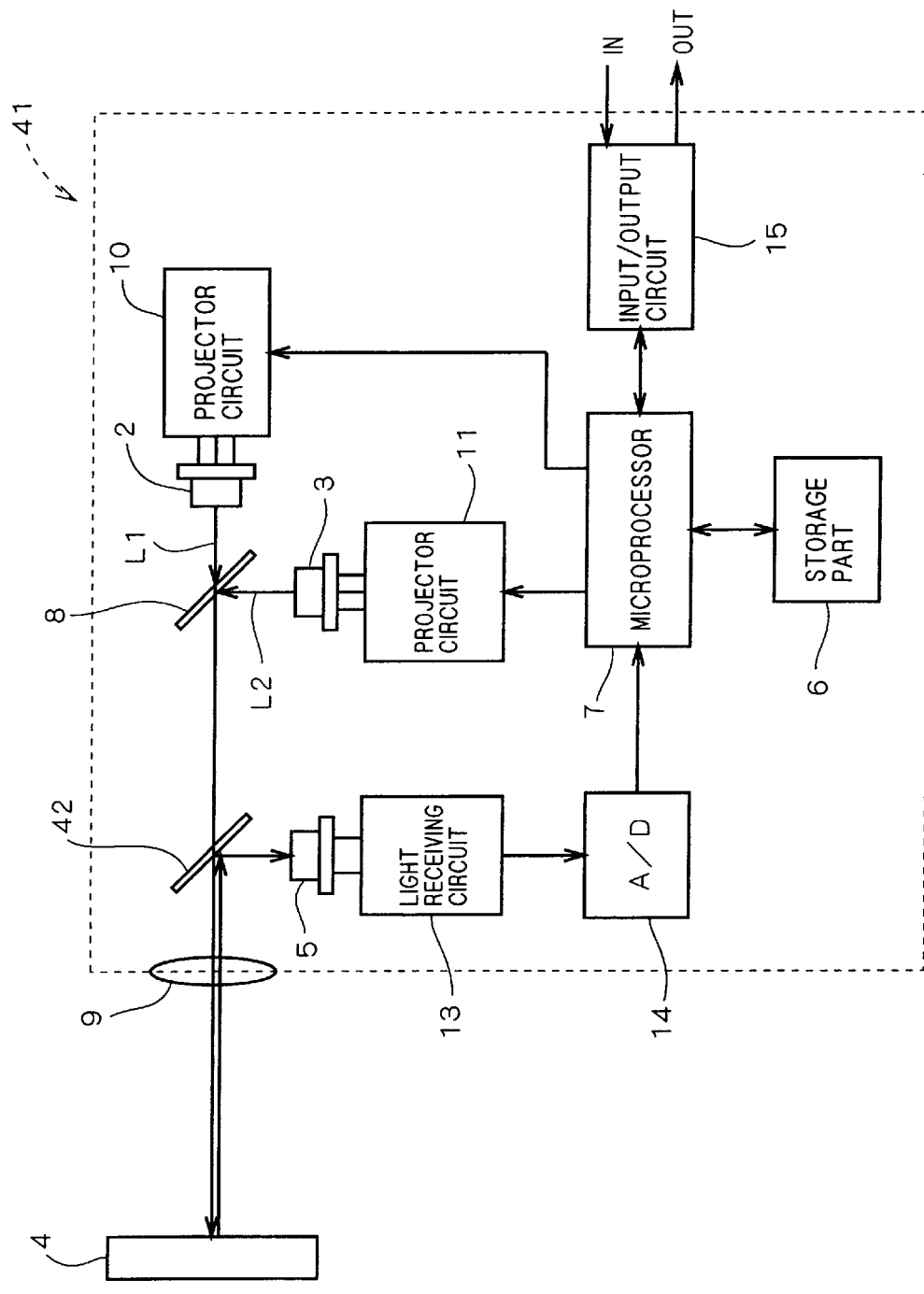
FIG. 14 is a diagram showing another modification of the plastic identifying apparatus according to the first preferred embodiment.
Figure 15:
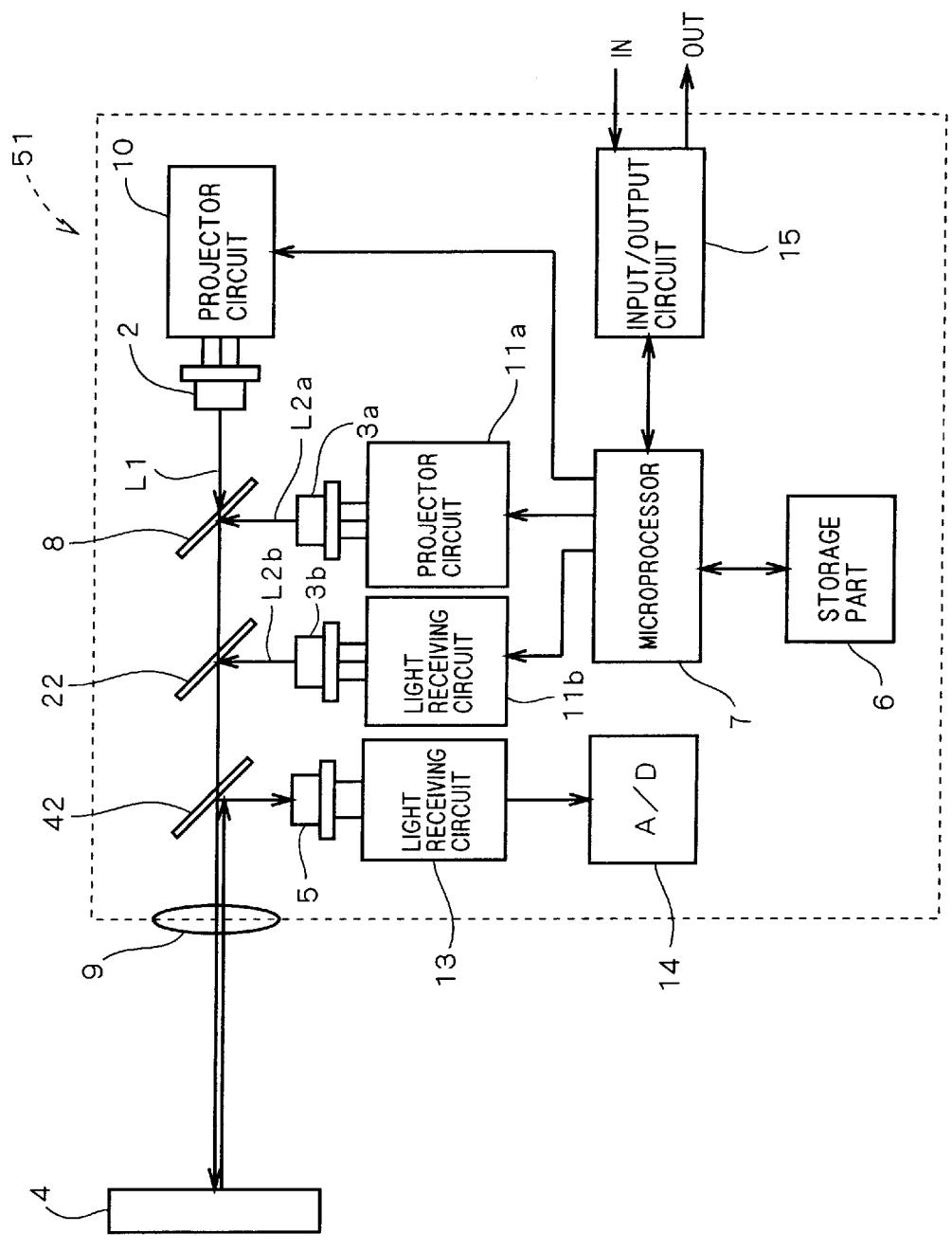
FIG. 15 is a diagram showing another modification of the plastic identifying apparatus according to the second preferred embodiment.

As a still other modification of the plastic identifying apparatuses 41 and 51 shown in FIGS. 14 and 15, an optical fiber is interposed on the optical path between the projector lens 9 and the object to be identified 4, the irradiation light and transmitted light on the optical path therebetween may be transferred by the optical fiber.

As a modification of the plastic identifying apparatuses 1, 21, 31, 41 and 51 shown in FIGS. 11 to 15, the light of which wavelength is in the range of 1500 to 1760 nm may be used as the reference light L1. In this case, when the wavelength of the reference light L1 exceeds 1640 nm, it may be suitably changed according to the situation as to which light of the above-mentioned plural lights that the light source irradiates (L1, L2, L2a, L2b) should be used for the reference light L1 or the detecting light L2, L2a, L2b.

Note that according to the plastic identifying apparatuses 1, 21, 31, 41 and 51 according to the foregoing preferred embodiments and modifications, not only existing plastics such as the mentioned seven plastics, but new plastics to be made in the future can be identified.

While the preferred embodiments of the invention has been described, it is to be understood that the scope of the invention is not limited to the foregoing preferred embodiments but defined by the accompanying claims.

What is claimed is:

1. A plastic identifying apparatus (1, 21, 31, 41, 51) to identify by what type of plastic in predetermined plural types an object made of plastic to be identified (4) is formed, characterized by comprising:

a light source (2, 3, 3a, 3b) irradiating to said object to be identified a detecting light (L2, L2a, L2b) of which wavelength is in an absorption wavelength band to increase the light absorptance of at least one type plastic in said plural types, and a reference light (L1) of which wavelength is different from said wavelength of said detecting light;

a light receiving means (5, 5a, 5b, 5c) receiving a transmitted light or reflected light of said reference light and said detecting light from said object to be identified, and outputting a reference value expressing the quantity of light received of said reference light and a detecting value expressing the quantity of light received of said detecting light; and an identifying means (7) computing a proportion of or difference between said reference value and said detecting value, and identifying, based on the computed value, by what type of plastic in said plural types said object to be identified is formed.

2. The plastic identifying apparatus according to claim 1, characterized in that said light source comprises:

a first semiconductor light-emitting device (2) emitting said reference light; and a second semiconductor light-emitting device (3) emitting said detecting light.

3. The plastic identifying apparatus according to claim 2, characterized in that said first semiconductor light-emitting device and said second semiconductor light-emitting devices are respectively formed by a laser diode.

4. The plastic identifying apparatus according to claim 2, characterized in that said first semiconductor light-emitting device and said second semiconductor light-emitting devices are respectively formed by a light emitting diode.

5. The plastic identifying apparatus according to claim 1, further comprising a storing means (6) in which plural reference values that respectively correspond to said plural types of plastics are stored, characterized in that:

said identifying means identifies that said object to be identified is formed by plastic of the type corresponding to said reference value closest to said computed value in said plural reference values stored in said storing means.

6. The plastic identifying apparatus according to claim 1, characterized in that the wavelength of said reference light is in a wavelength region in which the light absorptances of all the types of plastics in said plural types are of substantially the lowest level.

7. The plastic identifying apparatus according to claim 1, characterized in that the wavelength of said detecting light is in an infrared light region having a longer wavelength than 1600 nm.

8. The plastic identifying apparatus according to claim 1, characterized in that the wavelength of said detecting light is in the range of 1700 to 1760 nm or 1640 to 1700 nm.

9. The plastic identifying apparatus according to claim 1, characterized in that the wavelength of said reference light is in the range of 1500 to 1600 nm.

10. The plastic identifying apparatus according to claim 1, characterized in that the wavelength of said reference light is in the range of 1500 to 1760 nm.

11. The plastic identifying apparatus according to claim 8, characterized in that said identifying means identifies, based on said computed value, by which of polyethylene terephthalate and other type of plastic said object to be identified is formed.

12. A plastic identifying apparatus (21, 31) to identify by what type of plastic in predetermined plural types an object made of plastic to be identified (4) is formed, characterized by comprising:

a light source (2, 3a, 3b) irradiating to said object to be identified plural detecting lights (L2a, L2b) and a reference light (L1) of which wavelength is different from the wavelengths of said detecting lights;

a light receiving means (5, 5a, 5b, 5c) receiving a transmitted light or reflected light of said reference light from said object to be identified, and a transmitted light or reflected light of said detecting lights from said object to be identified, and outputting a reference value expressing the quantity of light received of said reference light and plural detecting values expressing the quantity of light received of said detecting lights; and an identifying means (7) computing a proportion of or difference between said reference value and each of said detecting values, and identifying, based on the computed value that said object to be identified is formed by what type of plastic in said plural types, and in that:

the wavelengths of said detecting lights are in an absorption wavelength band to increase the light absorptance of at least one type of plastic of said plural types and are different from each other.

13. The plastic identifying apparatus according to claim 12, characterized in that the wavelength of said reference light is in a wavelength region in which the light absorptances of all the types of plastics in said plural types are of substantially the lowest level.

14. The plastic identifying apparatus according to claim 12, characterized in that the wavelengths of said plural detecting lights are in an infrared light region having a longer wavelength than 1600 nm.

15. The plastic identifying apparatus according to claim 12, characterized in that said plural detecting lights that said light source irradiates contains at least a first light of which wavelength is in the range of 1700 to 1760 nm, and a second light of which wavelength is in the range of 1640 to 1700 nm.

16. The plastic identifying apparatus according to claim 12, characterized in that the wavelength of said reference light is in the range of 1500 to 1600 nm.

17. The plastic identifying apparatus according to claim 12, characterized in that the wavelength of said reference light is in the range of 1500 to 1760 nm.

18. A plastic identifying apparatus (1, 21, 31, 41, 51) to identify by what type of plastic in predetermined plural types an object made of plastic to be identified (4) is formed, characterized by comprising:

a light source (2, 3, 3a, 3b) capable of irradiating plural lights (L1, L2, L2a, L2b) of which wavelengths are in an absorption wavelength band to increase the light absorptance of at least one type of plastic in said plural types and are different from each other, and irradiating one of said plural lights as a reference light (L1) to said object to be identified and irradiating at least one light of the rest in said plural lights as a detecting light (L2, L2a, L2b) to said object to be identified;

a light receiving means (5, 5a, 5b, 5c) receiving a transmitted light or reflected light of said reference light and said detecting light from said object to be identified, and outputting a reference value expressing the quantity of light received of said reference light and a detecting value expressing the quantity of light received of said detecting light; and an identifying means (7) computing a proportion of or difference between said reference value and said detecting value, and identifying, based on the computed value, by what type of plastic in said plural types said object to be identified is formed.

19. The plastic identifying apparatus according to claim 18, characterized in that it is changeable as to which light of said plural lights irradiated by said light source is used as said reference light or said detecting light.

20. A plastic identifying method of identifying by what type of plastic in predetermined plural types an object made of plastic to be identified (4) is formed, characterized by comprising the steps of:

a light irradiating step of irradiating to said object to be identified, by a predetermined light source (2, 3, 3a, 3b), a detecting light (L2, L2a, L2b) of which wavelength is in an absorption wavelength band to increase the light absorptance of at least one type of plastic in said plural types, and a reference light (L1) of which wavelength is different from said wavelength of said detecting light;

a light receiving step of receiving by a predetermined light receiving means (5, 5a, 5b, 5c) a transmitted light or reflected light of said reference light and said detecting light from said object to be identified, and outputting to said light receiving means a reference value expressing the quantity of light received of said reference light and a detecting value expressing the quantity of light received of said detecting light; and an identifying step of computing a proportion of or difference between said reference value and said detecting value, and identifying, based on the computed value, by what type of plastic in said plural types said object to be identified is formed.

21. A plastic identifying method of identifying by what type of plastic in predetermined plural types an object made of plastic to be identified (4) is formed, characterized by comprising the steps of:

a light irradiating step of irradiating to said object to be identified, by a predetermined light source (2, 3a, 3b), plural detecting lights (L2a, L2b) of which wavelengths are in an absorption wavelength band to increase the light absorptance of at least one type plastic in said plural types, and a reference light (L1) of which wavelength is different from said wavelengths of said detecting lights;

a light receiving step of receiving by a predetermined light receiving means (5, 5a, 5b, 5c) a transmitted light or reflected light of said reference light and said detecting lights from said object to be identified, and outputting to said light receiving means a reference value expressing the quantity of light received of said reference light and plural detecting values expressing the quantity of light received of said detecting lights; and an identifying step of computing a proportion of or difference between said reference value and each of said detecting values, and identifying, based on the computed value, by what type of plastic in said plural types said object to be identified is formed.

* * * * *